(12) United States Patent
Davis et al.

(10) Patent No.: US 7,259,278 B2
(45) Date of Patent: Aug. 21, 2007

(54) ANTI-S-PHASE TUBULIN LIGANDS

(75) Inventors: Ashley Stuart Davis, Denver, CO (US); Kim Maria Middleton, Denver, CO (US); Jain Dong Jiang, New York, NY (US); J. George Bekesi, New York, NY (US)

(73) Assignee: Cytoskeleton Inc., Denver, CO (US)

( * ) Notice: Subject to any disclaimer, the term of this patent is extended or adjusted under 35 U.S.C. 154(b) by 395 days.

(21) Appl. No.: 09/725,030

(22) Filed: Nov. 29, 2000

(65) Prior Publication Data

US 2002/0065229 A1     May 30, 2002

(51) Int. Cl.
*C07C 237/28* (2006.01)
(52) U.S. Cl. .............. 564/161; 560/8; 562/405
(58) Field of Classification Search .............. 564/161; 560/8; 562/553, 405
See application file for complete search history.

(56) References Cited

OTHER PUBLICATIONS

Jiang Cancer Research 58, 2126, 1998.*
Jiang J D, Cancer Research 58 (23) 5389□95, 1998.*
Alberts The Molecular Biology of the Cell, 2nd Ed., 1989, pp. 727-786.*
Abraham I., Proc Natl. Acad. Sci. 83, 6839-43, 1986.*
Sorger P.K., Curr Opin Cell Biol. 9, 807-814, 1997.*
Jordan, Current Opinion in Cell Biology 10 (1) 123-30, 1998.*
Fang X. (Biochemical Journal 352 Pt 1 135 42, 2000).*
Steiner M. R. (Annals of the New York Academy of Sciences 95 132 41, 2000).*
Tsuchiyama Y (Kidney International 58 (5) 1941-52, 2000).*
Urbani C., Tropical medicine & international health : TM & IH, (Nov. 2001) 6 (11) 935-44.*
Kerboeuf Dominique, International journal of antimicrobial agents, (Sep. 2003.) 22 (3) 332-46.*
Wolstenholme Adrian J., Trends in parasitology, (Oct. 2004) 20 (10) 469-76.*
Miljutin, D. M., Nematology, (2001) vol. 3, No. 6, pp. 491-502.*
A. Davis et al. Novel suicide ligands of tubulin arrest cancer cells in S-phase. Neoplasia, 1 (6), p. 498-507. 1999.
Jaing J.D. et al. Synthesis, cancericidal and anti-microtubule activities of 3-haloacetamido-benzoyl-ureas. Anti-Cancer Drug Design, 13 (7), p. 735-747. 1998.

* cited by examiner

*Primary Examiner*—David Lukton
(74) *Attorney, Agent, or Firm*—Cozen O'Connor, P.C.

(57) ABSTRACT

It is presently accepted that the mechanism of action for all anti-tumor tubulin ligands involves the perturbation of microtubule dynamics during the G2/M phase of cell division and subsequent entry into apoptosis (1). In this invention, we report a novel tubulin ligands which have a unique mechanism of action. These compounds, halogenated derivatives of acetamido benzoyl ethyl ester (HAABE), arrest cancer cells in S-phase and cause cell death by a combination of apoptosis (DNA ladder) and necrosis (DNA degradation) type mechanisms. Normal cells are not affected at the same concentrations of compound. The ligands bind covalently to tubulin in vitro and in vivo and shows potent cancericidal activity in tissue culture assays and in animal tumor models. These compounds target early S-phase at the G1/S transition rather than the G2/M phase and mitotic arrest. Bcl-2 phosphorylation, a marker of mitotic microtubule inhibition by other tubulin ligands was dramatically altered, phosphorylation was rapid and biphasic rather than a slow linear event. The halogenated ethyl ester series of derivatives thus constitute a unique set of tubulin ligands which induce a novel mechanism of cancer cell death.

10 Claims, 11 Drawing Sheets a.

3-Haloacetamido benzoyl ethyl ester b.

3-Haloacetamido benzoylurea

Figure 8

| Halogen | MW | Microtubule Assembly IC50 (uM) | Cancer Cell Cytotoxicity ID50 (uM) |
|---------|-----|-------------------------------|-----------------------------------|
| F | 233 | >100 | >79 |
| Cl | 241 | >100 | 7.7 |
| Br | 253 | 10 | 1.9 |
| I | 271 | 2.5 | 0.17 |

Figure 9

| Human Tissue Type | Cell Line | Cytotoxicity (ug/ml) | |
|---|---|---|---|
| | | ID50 | ID90 |
| T-cell Leukemia | CEM | 0.047 | 0.1 |
| Myelodisplasia Syndromes | Sp | 0.085 | 0.25 |
| Melanoma | DND-1A | 0.25 | 0.51 |
| Renal Cancer | 786-0 | 0.042 | 0.08 |
| Breast Cancer | MCF-7 | 0.12 | 0.49 |
| Non-small Cell Lung Cancer | NCI-H522 | 0.05 | 0.09 |
| Colon Cancer | HCT-116 | 0.09 | 0.41 |
| Lymphoma | Daudi/wt* | 0.007 | 0.05 |
| Lymphoma | Daudi/MDR* | 0.005 | 0.06 |
| Normal Lymphocytes | PHA stimulated** | 2.5 | 5.5 |

Figure 10

| Tumor* | Treatment | Number of mice | Therapeutic regime | Tumor bearing mice** (tumor volume**) | Tumor free mice** |
|---|---|---|---|---|---|
| Murine EL4 Lymphoma (s.c. implant) | Solvent | 15 | s.c. injection on day 4,6,8,11,13 | 15 (2731+/-807) | 0 |
| Murine EL4 Lymphoma (s.c. implant) | BAABE | 15 | s.c. injection on day 4,6,8,11,13 | 3 (1064+/-411) | 12 |

Figure 11

| Compound | Dose (mg/kg) | Treatment Schedule | TI% | TF/T |
|---|---|---|---|---|
| Control | Diluant* | i.v. day 1,2,3 | 0 | 0/10 |
| 3-IAABE | 15 | i.v. daily x4 x2 | 43 | 0/10 |
| 3-IAABE | 25 | i.v. 1,2,3 | 85 | 2/10 |
| Paclitaxel | 30 | i.v. q3 x3 | 90 | 0/10 |
| Vinblastine | 3 | i.v. q6d x3 | 80 | 0/10 |

ANTI-S-PHASE TUBULIN LIGANDS

FIELD OF THE INVENTION

Tubulin is an intra-cellular protein that polymerized to form structural components of the cytoskeleton called microtubules. Typical tubulin ligands such as colchicine, paclitaxel, vinblastine, epothilones, halicondrins, benomyl and mebendazole directly inhibit cell division by binding to tubulin which subsequently arrests cells in mitosis. This is the basis of their therapeutic value, such as treating gout with colchicine, restenosis with paclitaxel, cancer with paclitaxel, vinblastine, epothilones and halichondrins, and fungal infections with benomyl and malaria and helminths with mebendazole. We have developed two compounds which set two new precedents for tubulin ligands. First, they covalently bind to tubulin creating a stable conjugate that inhibits tubulin polymerization. And second; they arrest cells in the S-phase of the cell cycle. We have shown that there is therapeutic potential for these ligands and their novel characteristics such as low resistant cell line generation rates and short exposure time make them ideal for therapeutic regimes where side effects of chemotherapy are a major issue.

DISCUSSION OF THE BACKGROUND ART

This description focuses mainly on the research described in a recent article published by the inventors (ref. 1.1, Novel suicide ligands of tubulin arrest cancer cells in S-phase. A Davis, J-D Jaing, K M Middleton, Y Wang, I Weisz, Y-H Ling and J G Bekesi, Neoplasia, 1, (6), 498–507, 1999). This description does not include the regimes for synthesizing the core compound which are previously published (ref. 1.2, Anticancer Drug Design 1998) and patent pending (U.S. patent application Ser. No. 09/258,732). The synthesis of iodine acetamido benzoyl ethyl acetate was performed by Imre Weisz, Mount Sinai School of Medicine, N.Y. in August 1998 and is not yet published.

Tubulin and microtubules are important targets for anticancer drug development. The first FDA approved anticancer tubulin ligands were the vinca-alkaloids which showed therapeutic potential against lymphoma and leukemia (1.3,2). The vinca alkaloids appear to target tubulin and microtubules because of their specificity measured in biochemical assays (3,4) and their affects on microtubule structure in vivo (5,6). Vinca alkaloids are known to depolymerize microtubules in vitro. In contrast, paclitaxel stabilizes microtubules in vitro and in vivo (7,8). Paclitaxel was recently approved for the treatment of ovarian and breast cancer (9,10). The presently accepted mechanism of action is that all anti-tumor tubulin ligands affect dynamic microtubule structures which are most sensitive during mitosis (1.3,11). Subsequent arrest at mitosis induces the apoptotic mechanism to cause cell death. We had been studying small molecular weight compounds that interact with tubulin and require straight forward synthesis with a view to develop them as anti-cancer agents (12,13). This article describes the novel finding that the haloacetamido benzoyl ethyl ester (HAABE) derivatives (FIG. 1a) are acting via tubulin and that these tubulin ligands can uniquely arrest cancer cells in the G1/S cell cycle transition. Optimization of the HAABE series of compounds resulted in the iodine derivative (IAABE) which has a high therapeutic potential for a variety of cancer types.

SUMMARY OF THE INVENTION

We have developed novel anti-tubulin ligands that bind covalently to tubulin and have desirable characters for therapeutic candidates. For example, cells grown in low concentrations of these compounds do not develop resistance (ref: Jain-Ding Jaing to be published and ref: 33). Other advantages include high affinity and specificity. In addition, the HAABE derivatives differ significantly with respect to other covalently modifying tubulin ligands, especially on cancericidal index, tubulin polymerization profiles, bcl-2 inactivation, cell cycle, DNA synthesis and mitochondrial permeability transition pore complex activation. Finally, the fact that IAABE has a cancericidal index of 500 means that this compound is approaching the efficacy often associated with anti-microbial compounds. Future anti-cancer drug development programs will focus on novel mechanisms to increase potency and decrease side effects, because of their quick absorption, rapid mechanism of action and high specificity we believe these compounds will become useful therapeutic agents for cancer treatment. In addition, the fact that so many other tubulin ligands have applications in anti-restenosis, anti-fungal, anti-helminths and anti-gout chemotherapics there is a strong likelihood that BAABE and IAABE will likewise have potential in these areas. In support of this hypothesis it was recently found that IAABE has anti-trypanosome activity (ref: Dr. J G Bekesi 1999), following this argument other diseases may be treatable with these compounds.

DESCRIPTION OF FIGURES

FIG. 8. Activity of the halogenated acetamido benzoyl ethyl ester F, Cl, Br and I series on microtubule polymerization and cancer cell cytotoxicity. $IC_{50}$, concentration for 50% inhibition of microtubule polymerization. $ID_{50}$, concentration for 50% cell death of CEM cancer cells. MW, molecular weight in daltons.

FIG. 9. Cytotoxicity of IAABE against different tumor cells. $ID_{50}$ and $ID_{90}$, see Table 1 for definitions, and references 12,13,42 and 43 for cell line origins.*—Daudi/MDR are PGP+ cells, and Daudi/wt are PGP-cells (13). **—Normal human lymphocytes were pretreated with 1 µg/ml phytohemagglutinin for 24 h at 37° C. in order to induce proliferation.

FIG. 10. Murine lymphoma inhibition by BAABE.
* —Murine EL4 lymphoma was implanted (s.c.) into C57 mice.
** —Tumor volume was determined at T=35 days using the formula: $w^2L(Pi/6)$; w=width, L=length and Pi=3.142.

FIG. 11. Prostate carcinoma inhibition by IAABE.
* —N,N-dimethylacetamide, propylene glycol and Tween 80 (1:2:1 v/v/v)
1 —$2.5\times10^6$ tumor cells were injected s.c. on day 0, treatment started at day 1.
2 —TI%=Tumor growth inhibition 1 week after last treatment.
3 —TF/T=Tumor free mice at day 90 after tumor implant.

DETAILED DESCRIPTION OF THE INVENTION

Methods

Figure 1:
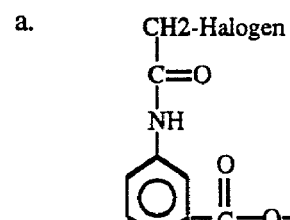
FIG. 1. Core structure of compounds. Structure of halogenated acetamido benzoyl ethyl ester (A) and halogenated acetamido benzoyl urea (R) (Halogen=F, Cl, Br, I).
Figure 1:
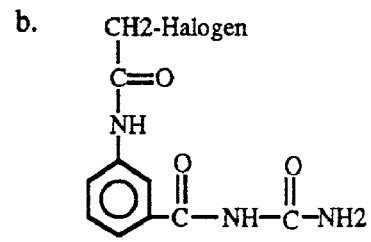

Cell culture. All cell lines were obtained from the American Type Culture Collection (Rockville, Md.) except human SP cells which were isolated from a biphenotypic leukemic cell line (34,35). CEM cells were cultured to Iscove's Dulbecco's medium with 10% FCS, penicillin and streptomycin (250 unit/ml each). SP cells were cultured in minimal Eagle's medium with 10% FBS. Daudi, DND-1A, 786-O, MCF-7, NCI-H521 and HCT-116 cell lines were cultivated in RPMI 1640 plus 10% FBS. PBLs were cultured in RPMI 1640 plus 10% homologous plasma. All cell lines were cultured in a humid chamber at 37° C. with 5% CO2.

FACS analysis. DNA content was measured using a Cycle TEST kit (Becton Dickinson, San Jose, Calif.). Light scattering and DNA luminescence were measured with a FAC-Scan flow cytometer (Becton Dickinson) and software Cell-fit and Cell Quest (Becton Dickinson). Approximately 1000 and 5000 cells were counted from a preparation of $1\times10^6$ cells.

Microtubule polymerization assays. The CytoDYNAMIX Screen 01 (Cytoskeleton Inc. Denver, Colo.) was utilized to measure microtubule polymerization. The compounds were pipetted directly into each well of the 96-well plate placed on ice and using G-PEM buffer as diluent (80 mM PIPES pH 6.9, 1 mM MgCl2, 1 mM EGTA and 1 mM GTP). Each well contains G-PEM buffer, compound at the concentration stated and MAP-rich tubulin at a concentration of 1 mg/ml. The plate is shaken orbitally for 20 s, warmed to 24° C. and the absorbance is read at 340 nm once every minute for 60 min. The tubulin is highly purified >99% MAP-rich tubulin with a high biological activity i.e. dynamic activity, which achieves >90% polymerization at 1.0 mg/ml (36). Previous assays (12) were performed using impure, low activity tubulin from Sigma Chemical Company (St. Louis, Mo.) which is approximately 50% pure and has less than 20% polymerization activity (36).

Tubulin labeling. Tritium labeled iodine acetamido benzoyl ethyl acetate (IAABE) was produced by Moraveck Biochemical Inc. (Brea, Calif.) to a specific activity of 25.5 Ci/mM. Pure tubulin (TL238 from Cytoskeleton Inc. Denver, Colo.) at 3 mg/ml in 5% glycerol—G-PEM was incubated with 5 µM tritiated IAABE for 60 min at 37° C. The control reaction tubulin and buffer reached a maximum $OD_{340nm}$ of 0.30 over 30 min. The labeling reaction OD never raised above $OD_{340nm}$ of 0.01. Cellular tubulin labeling experiments were performed the same as for cytotoxicity assays except 9 cm Petri dishes were used and tritium IAABE was substituted for IAABE. Cells were removed from the culture dish with trypsin EDTA treatment and the cells were centrifuged for 2 min at 2000 xg. Cell pellets were lysed in 1xSDS gel loading buffer containing 100 mM beta-mercaptoethanol, 1% SDS, 10% glycerol and 0.01% bromophenol blue. Pure tubulin and cell extracts were run on a 10% polyacrylamide gel and blotted onto nylon reinforced nitrocellulose membranes. Slices of the membranes were dissected and the radioactivity counted. Molecular weight was determined by comparison with colored molecular weight markers (Novex, Inc.).

Labeled tubulin for pinocytosis cell loading studies was produced as described above for radiolabeled tubulin, except non-tritiated IAABE was used at a concentration of 30 µM. The reaction products were then passed over a 30 cm G25 Sephadex column (Pharmacia Inc.) in G-PEM buffer, concentrated to 7.5 mg/ml and stored at −70° C. This removed all unbound IAABE and left pure tubulin drug covalent complex (TDCC).

Immunofluorescence staining of microtubule structure. CEM cells incubated in the presence or absence of IAABE were collected and centrifuged in a Cytospin centrifuge at 700 xg for 5 min. The slides were air dried and fixed with methanol at −20° C. for 20 min. The slides were incubated in PBS containing 1% BSA at 37° C. for 30 min. After washing with PBS for 3 min, cells on the slides were covered with 30 ul of antihuman beta-tubulin monoclonal antibody (4 ug/ml; Accurate Antibody, Westbury, N.Y.) and placed in a humid chamber at 24° C. for 60 min. The slides were washed with PBS three times for 3 min each, followed by staining with 10 ul of FTTC-labeled goat anti-mouse antibody (Coulter, Hialeah, Fla.) in a humid chamber at 24° C. for 60 min. After washing in PBS, the stained cells were visualized under a fluorescence microscope (model MC63, Zeiss, Jena, Germany).

Apoptotic DNA analysis. Soluble DNA from cells was extracted treating cells in lysis buffer (10 mM Tris-HCl pH8.0, 10 mM NaCl, 10 mM EDTA and 5% SDS) containing 1 ug/ml Proteinase-K for 1 h at 50° C. The mixture was extracted with phenol/chloroform and precipitated with 70% ethanol and pelleted by centrifugation 14000 xg for 10 min. The pellet was dried and resuspended in dH2O, the OD260/OD280 was >2.0, and the samples were treated with RNA$_{sc}$ 100 ng/ml for 20 min at 37C before running on 1% agarose gels in 1 x TBE. DNA ladders were stained with 100 ng/ml ethidium bromide and visualized under UV light.

DNA synthesis measurement. CEM cells at $2 \times 10^5$/ml were incubated with $ID_{90}$ concentration of the compound and $^3$H-thymidine (4 µCi/ml). Cells were harvested by vacuum filtration and filters were counted in scintillation fluid.

Bcl-2 analysis. Cells were treated with different concentrations of drugs for the time range between 0 and 24 h. Aliquots of cells were lysed in 50 mM Tris-HCl pH 7.4, 0.1% Triton X-100, 1% SDS, 250 mM NaCl, 15 mM MgCl2, 1 mM DTT, 2 mM EDTA, 2 mM EGTA, 25 mM NaF, 1 mM PMSF 10 ug/ml leupeptin and 10 ug/ml aprotinin. The protein concentration was determined by a DC protein assay kit (Biorad). Equal amounts of protein were subjected to electrophoresis in 0.1% SDS and 10% polyacrylamide gels. Proteins were blotted onto nitrocellulose and blocked with 5% non-fat milk TBST buffer. Bcl-2 was detected by probing with bcl-2 MAb from Pharmingen, San Diego, Calif.

Mitochondrial permeability transition assay. The method of Constatini et al. (1995)(21) was used to measure mitochondrial permeability transition. Briefly, mitochondria are isolate from liver by homogenization in ice cold homogenization buffer 0.25 M sucrose, 10 mM Tris-HCL pH 7.4 and 0.1 mM EGTA. Unbroken cells and cell debris was removed by centrifugation at 650 xg for 10 min. Mitochondria were pelleted by centrifugation at 8000 xg for 10 min, and washed twice by resuspension in homogenization buffer and centrifugation at 8000 xg for 10 min. Mitochondria were diluted to 0.5 mg/ml protein in swelling buffer 0.20 M sucrose, 10 mM Tris-MOPS pH 7.4, 5 mM Tris-succinate, 1 mM Tris-phosphate, 10 µM Tris-EGTA, 2 µM rotenone). Calcium chloride 15 µM was used to sensitize the permeability pore complex. Mitochondria in swelling buffer were pipetted into the same buffer containing the compound of interest. Absorbance was measured over 20 min at $OD_{540mm}$, absorbance is inversely proportional to swelling extent.

Cell loading studies. The method of Okada and Rechsteiner (1982)(27) was used to load CEM cells with tubulin or TDCC using the Influx™ Pinocytic Cell Loading Reagent (Molecular Probes Inc. Portland, Oreg.). Briefly, $4 \times 10^6$ cells were incubated in 20 ul hypertonic loading medium plus 20 ul of tubulin or TDCC at 7.5 mg/ml protein for 10 min at 37° C., followed by adding 1 ml of hypotonic lysis medium for 1.5 min at 37° C. Cells were finally incubated in 16 ml of normal tissue culture medium. Samples were then processed for FACS analysis.

Cytotoxicity assays. Cells in suspension were seeded into 96-well plates at $10^5$ cells/well, and the compounds added, total well volume was 250 µl. Cells were cultured for 48 h and the viability measured by trypan blue exclusion. $ID_{50}$ and $ID_{90}$ values were determined by the concentration of compound required to induce cell death in 50 or 90% of cells respectively.

RESULTS

Figure 2:
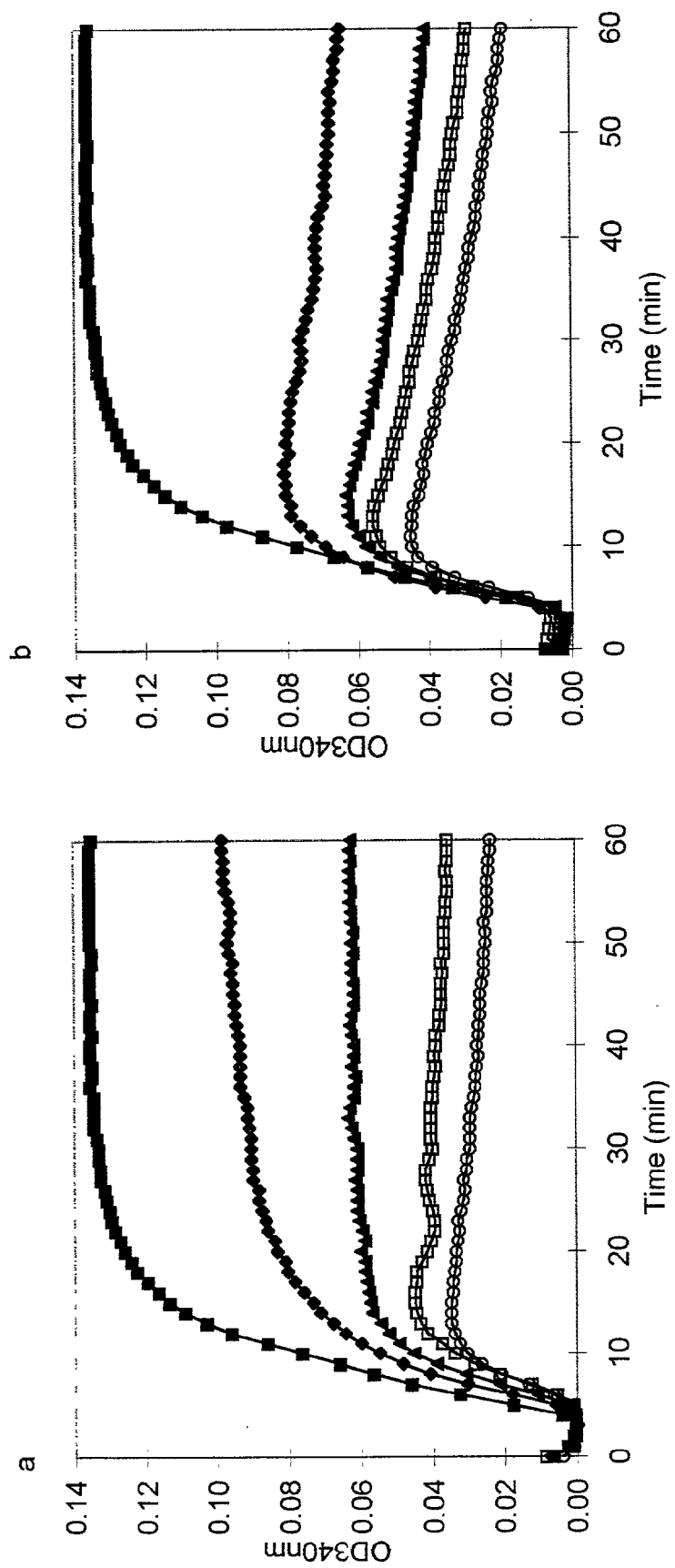
FIG. 2. Microtubule polymerization inhibition by IAABE and BAABE. Compounds were dissolved in G-PEM buffer at 4° C. prior to resuspending the lyophilized tubulin in the wells of a 96-well plate (CytoDYNAMIX Screen 01, Denver, Colo., USA). Absorbance was measured over time, absorbance is proportional to microtubule content. $IC_{50}$ values were determined by linear regression analysis of concentration versus percent inhibition, concentration at 50% inhibition at 60 min was defined as the $IC_{50}$. Concentrations of IAABE (A) were 0 (■), 1.0 (♦), 2.5 (▲), 5.0 (□) and 10 µM (○). Concentrations of BAABE (B) were 0 (■), 10 (♦), 20 (▲), 40 (□) and 80 µM (○).

We had previously shown that the halogenated acetamido benzoyl urea (HAABU) series of compounds (FIG. 1b), strongly inhibited microtubule polymerization (12,13), however our initial examination of the closely related HAABE compounds showed no effects on microtubules (12). Therefore, we decided to repeat the microtubule polymerization study using an optimized assay procedure. The CytoDYNAMIX™ Screen system (see methods) was utilized to test activity of these derivatives against tubulin polymerization. Using this system, we detected significant microtubule inhibition with two of the HAABE compounds (BAABE and IAABE; FIGS. 2a,b). There was a proportional relationship between the size of the halogen and inhibition of microtubule assembly (Table 1). The derivatives with the smallest halogens, fluorine and chlorine, did not inhibit microtubule assembly when present at 100 µM. Whereas the bromine and iodine derivatives had $IC_{50}$ values of 30 and 2.5 µM respectively. One peculiarity of the microtubule inhibition activity was a decline in polymerization after a short time in the presence of compound. In particular, BAABE and IAABE showed this response (see FIGS. 2a,b at >15 min). It was hypothesized that this affect could be due to increased GTPase activity, polymer binding activity, slow binding kinetics, or by nucleophilic attack causing a covalent modification of monomeric tubulin as would be expected by the more reactive bromine and iodine derivatives. Subsequent experiments showed the latter hypothesis to be correct.

Figure 3:
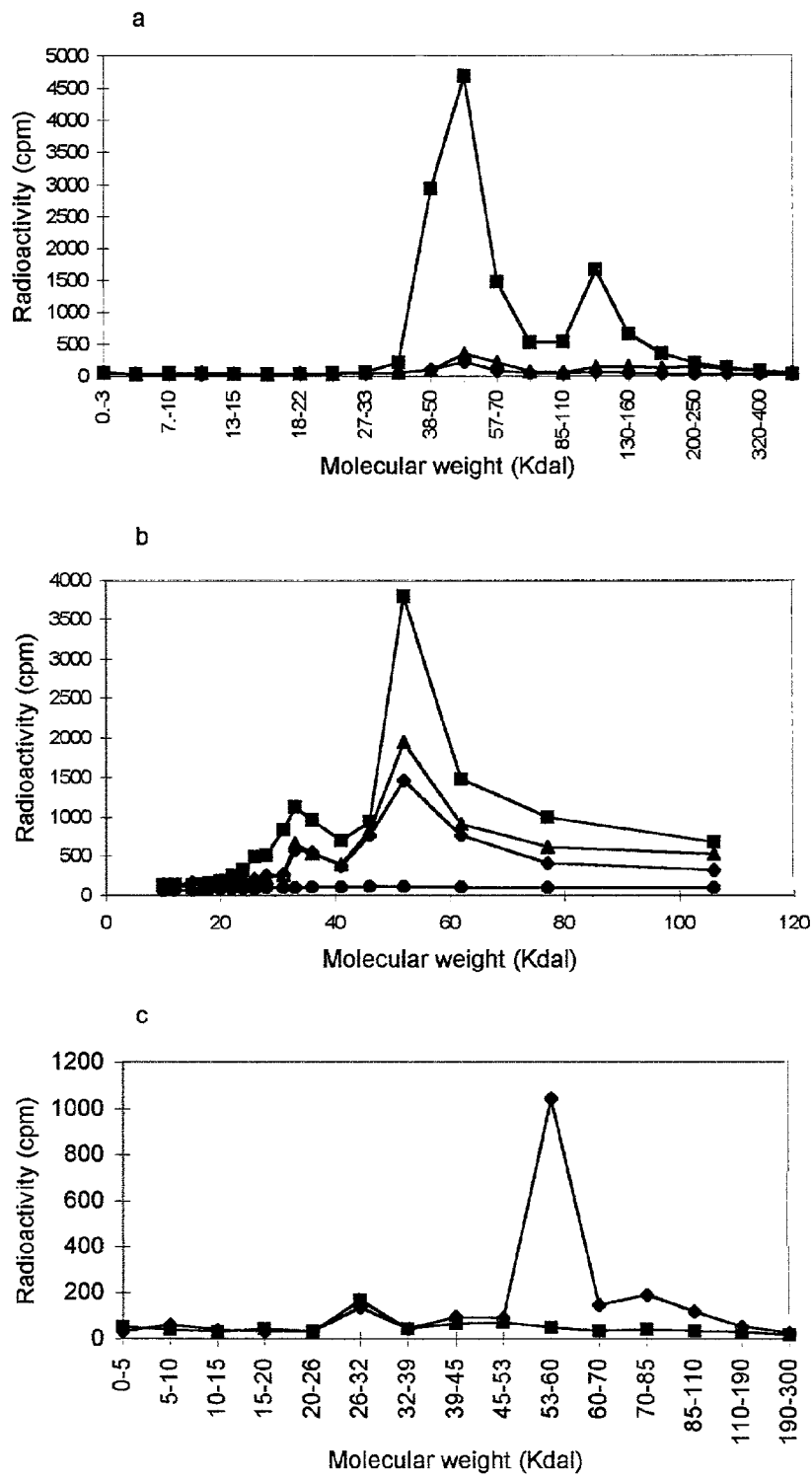
FIG. 3. Covalent modification of tubulin by IAABE. A, Tubulin or BSA were incubated in the presence of $^3$H-IAABE for 0 min (▲ tubulin) or 60 min (■ tubulin; ♦ BSA). Samples were separated on a polyacrylamide gel and blotted onto a nitrocellulose membrane. Lanes were dissected into slices and counted for radioactivity. Tubulin is molecular weight 55 Kdal and BSA is 68 Kdal. The peak at 55 Kdal is monomeric tubulin and the peak at 120 Kdal represents tubulin dimers. B, CEM cells were incubated in the presence of 0.37 µM $^3$H-IAABE for 0 (●), 1 (■), 4 (▲), and 12 h (♦). Cells were harvested and lysed directly into gel loading buffer. Samples were separated on a polyacrylamide gel and blotted onto a nitrocellulose membrane. Lanes were dissected into slices and counted for radioactivity. Note major peak at 55 Kdal. C, DEAE purification of $^3$H-IAABE labeled tubulin from CEM cells. Extracts from $^3$H-IAABE treated cells (1 h incubation) was purified with the DEAE method. Bound tubulin (♦) and unbound fractions (■) were blotted and counted as described above. Note that 95% of radioactivity co-eluted with the tubulin.

IAABE was labeled with tritium and incubated with either pure tubulin or pure BSA. Highly specific labeling was found to be associated with tubulin, whereas bovine serum albumin (BSA) did not label in the same assay (FIG. 3a). The stoichiometry of tritium labeled IAABE binding to tubulin was found to be 0.05:1.0 (IAABE:tubulin), this value is probably an underestimate due to quenching of tritium signal by the filter, also competitive assays with colchicine binding showed a stoichiometry of binding of 0.5:1.0 which indicates that a higher stoichiometry is possible. It is also possible that a sub-population of tubulin isotypes may be more reactive to nucleophilic attack even though non-covalent binding exists in all isotypes. Tritium labeled IAABE was also used to label cellular proteins by incubating with tissue culture cells. FIG. 3b shows that the label was rapidly incorporated (less than 1 h) into a protein of molecular weight of 55 Kdal which corresponds to the molecular weight of tubulin monomer. The amount of labeling subsequently declined over time probably because of protein metabolism and apoptosis associated proteolysis. We determined that IAABE was binding to tubulin in cells by purifying cellular tubulin with DEAE anionic exchange resin as previously used for determining vinblastine and colchicine binding to tubulin in cellular extracts (3,4). We found that 95% of the tritium label in the 55 Kdal area of the gel was co-eluted with the purified tubulin (FIG. 3c). These assays show that the majority of IAABE specifically labels tubulin and that tubulin is most likely the intracellular target. It is possible that cysteine is the modified aminoacid because first, in vitro the polymerization inhibition by IAABE is reduced in the presence of reducing agents (dithiothreitol and beta-mercaptoethanol, data reported elsewhere) and second the compound competes for the colchicine binding site (reported elsewhere) which is associated with cysteine residues (14).

Figure 4:
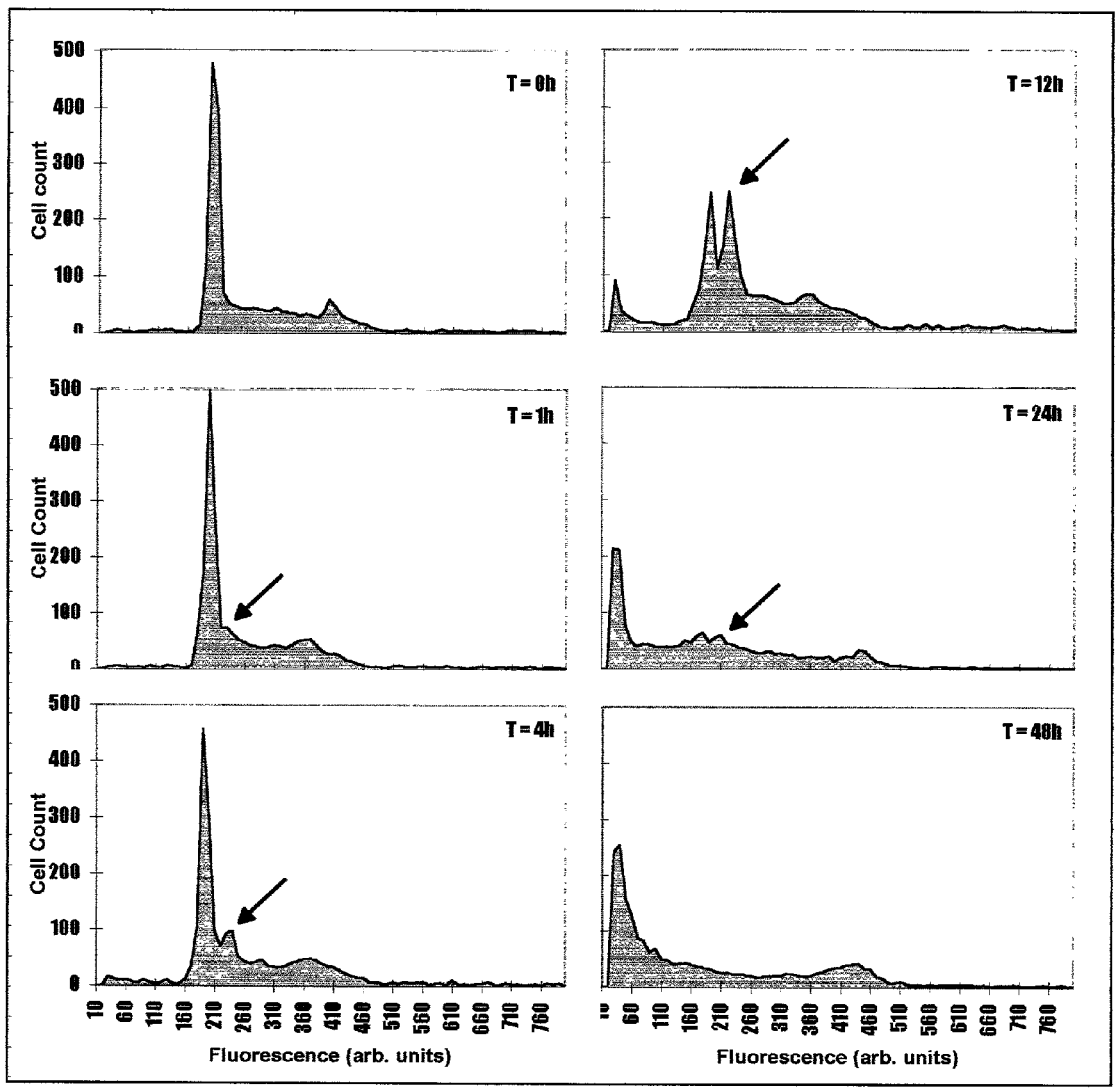
FIG. 4. Cell cycle arrest at G1/S transition in CEM cells treated with IAABE. CEM cells were seeded at $2\times10^5$/ml cells/ml in the presence of IAABE at the $ID_{90}$ concentration 0.37 µM. After 0 (A), 1 (B), 4 (C), 12 (D), 24 (E) and 48 h (F) samples were harvested and stained for DNA content (see methods) prior to FACS analysis. Experiments were performed twice with similar results. Approximately 1000 to 5000 cells were counted per sample. Note the peak at 2.3 n DNA (arrow) in the IAABE treated cells only.

The cell cycle was analyzed by flow cytometry of propidium iodide stained cells, IAABE (iodine derivative) treated cells began to show an elevated S-phase within 1 h of treatment. After 4 h, a sharp peak emerged in early S-phase of the G1/S transition, which contained approximately 2.3 n DNA (FIG. 4). The new peak became dominated in this cell population at 12 h. At this point, less than 1.0 n DNA was detected indicating DNA fragmentation. A slight G2/M elevation was also seen with IAABE over the time course of the experiment, but this was much less significant than that of early S-phase block. BAABE also caused this activity but with approximately five-fold less cells arresting at 2.3 n DNA. These responses are unique among tubulin ligands which usually arrest cells in G2/M phase (1). These responses differ from that of the HAABUs, vinblastine and paclitaxel, which cause cells to arrest characteristically in G2/M phase (4 n DNA), only later (>12 hrs) does the cell enter apoptosis (13,15,16). Biochemically, the IAABE treated cells were undergoing apoptosis with caspase pathway activation as early as the first hour of treatment (data reported elsewhere). In FIG. 4, the emergence of <2.0 n fragmented DNA follows after the 2.3 n arrest, the G2/M peak does not alter in height and is still present at T=48 h. This strongly suggests that the 2.3 n arrest is prior to the emergence of fragmented DNA and hence prior to apoptosis.

To investigate the mode of cell death we studied key diagnostic markers of apoptosis. The HAABU derivatives were shown to cause apoptosis by phenotypic observation, DNA fragmentation and bcl-2 phosphorylation (12,13) by a similar mechanism of known tubulin ligands such as paclitaxel and vinblastine (15,16,17). However, this was not the case with the HAABE derivatives. These compounds showed a unique mode of apoptosis.

Figure 5:
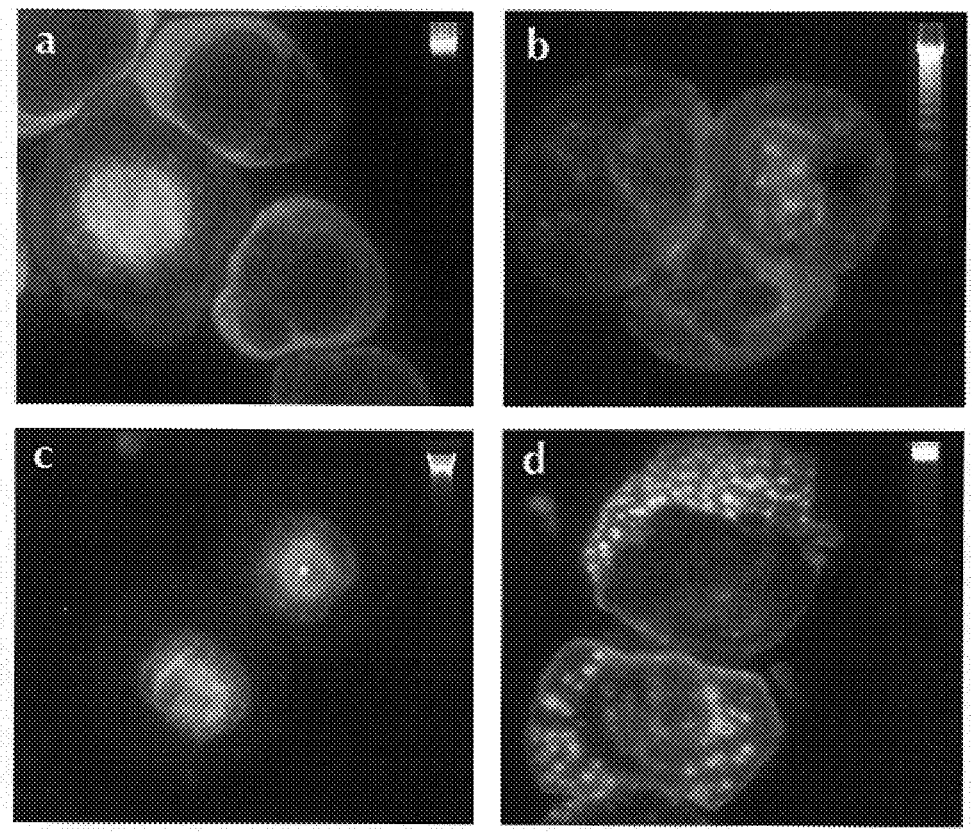
FIG. 5. Interferences with the formation of microtubule structure in IAABE treated CEM cells. All cells were treated with $ID_{90}$ concentration of compounds for 12 h (12,13). a—Untreated control cells, b—IAABE, c—Paclitaxel and d—Vinblastine. Insert is DNA extracted from the same samples run on 1% agarose gels and stained with ethidium bromide. Note absence of microtubule structure and appearance of apoptotic nuclei in IAABE treated cells. Note strong signal of apoptotic DNA ladder in IAABE treated cells compared to vinblastine and paclitaxel samples.

First, incubating cancer cells in the $ID_{90}$ concentration of IAABE shows absence of microtubule structures, the presence of nuclear apoptotic bodies, and DNA fragmentation occurred within 6 h. In contrast, paclitaxel shows dense mitotic spindle staining and vinblastine shows punctuated aggregates of tubulin, and both showed apoptotic DNA only after 12 h (FIG. 5).

Figure 6:
FIG. 6. The mode of cell death caused by IAABE. A, Analysis of Bcl-2 phosphorylation in CEM cells treated with IAABE, vinblastine or paclitaxel ($ID_{90}$ concentration of compounds) for 0, 1, 3, 6, 12 and 24 h (A,B,C,D,E and F respectively)(13). Note rapid appearance of phosphorylated bcl-2 (pBcl-2) in the IAABE samples. B, DNA synthesis inhibition determined by $^3$H-thymidine uptake measurements. Cells were incubated with $ID_{90}$ of the compound (25). +—Vinblastine; ▲—BAABU; ♦—IAABE, ■—BAABE. Note that IAABE and BAABE treated cells shut down DNA synthesis very soon after drug application compared to BAABU and vinblastine which have a slow linear decrease in thymidine incorporation. C, Effect of paclitaxel and IAABE on mitochondrial permeability transition. Mitochondria were incubated at 24° C. in 15 µM CaCl2 in the presence of paclitaxel or IAABE (30). Concentration of paclitaxel were 0 (■), 5 (●), 10 (□), 20 (∆) and 40 µM (○). Concentrations of IAABE were 0 (■) and 1 mM (♦). Absorbance is inversely proportional to mitochondrial swelling.
Figure 6:
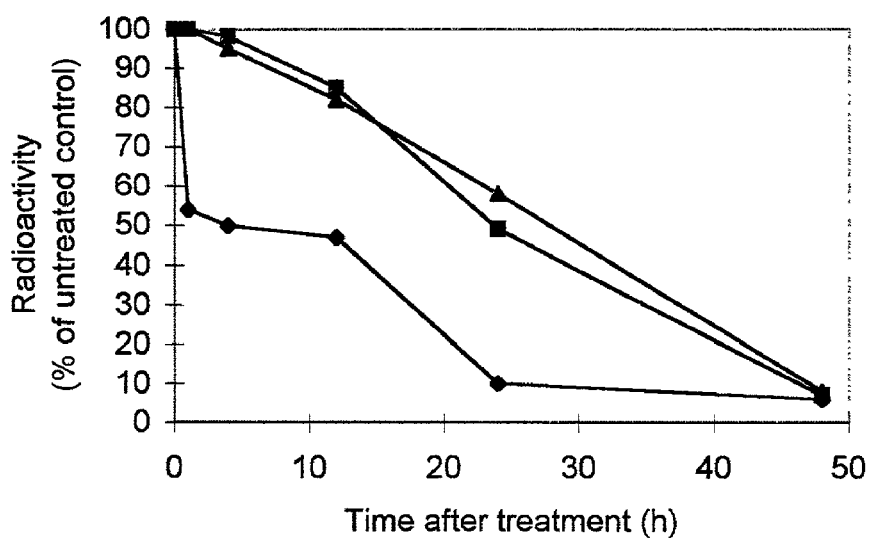
Figure 6:
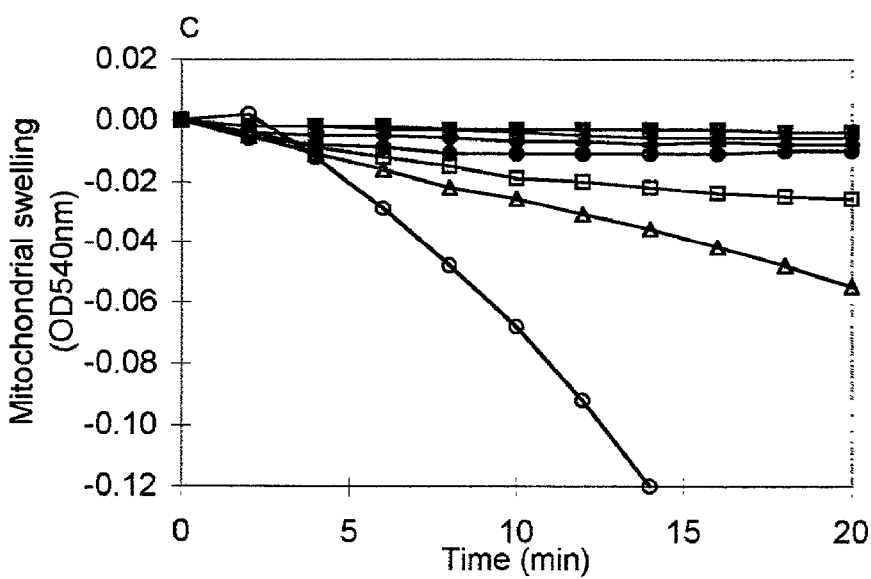

Second, in support of a novel apoptosis induction, we observed a unique time dependent profile of bcl-2 phosphorylation. Bcl-2 phosphorylation is associated with the activity of tubulin ligands. Raf1 kinase receives an unknown signal from the tubulin/microtubule cytoskeleton which induces it to phosphorylate bcl-2 (18). Bcl-2 is usually bound to the permeability transition pore complex of the mitochondria which suppresses pore opening and hence suppresses spontaneous apoptosis (19,20). Phosphorylated bcl-2 disrupts bax association thus causing an increased likelihood of apoptosis (15,18). Normally tubulin ligands increase the amount of phosphorylated bcl-2 only after 6 h, after this time point the amount of phosphorylated form increases linearly over time (17; FIG. 6a), however the IAABE derivative causes a biphasic response where the initial phosphorylation is very rapid (see 1 h time point, FIG. 6a). After 3 h, the relative proportion of phosphorylated bcl-2 then decreases with respect to the non-phosphorylated form, after 9 h the trend returns to a high ratio of phosphorylated bcl-2 at which point apoptosis is already occurring. It appears that the rapid uptake of IAABE and labeling of tubulin within an hour (FIG. 3b) causes a rapid response in cell signaling pathways, which results in induction of apoptosis before mitotic block.

Third, using the $^3$H-thymidine incorporation assay, we found that cellular DNA synthesis was shut down immediately after the treatment with BAABE or IAABE (FIG. 6b), in agreement with the rapid appearance of early S-phase block induced by IAABE (FIG. 2) and BAABE. The kinetic profile of $^3$H-thymidine uptake of IAABE was remarkably different from those of vinblastine and BAABU (FIG. 6b), which caused a significant inhibition of DNA synthesis only after M-phase arrest i.e. greater than 12 h.

Fourth, the mode of cell death was further compared with that of paclitaxel by an assay to determine mitochondrial targeting (21), a key interface of the apoptotic process (22–23). Paclitaxel is known to increase the permeability of the mitochondria by interacting with a component (probably tubulin) on the outer membrane with a Kd of 5–20 μM (24). This process can be measured by following the absorbance change at 540 nm associated with mitochondrial swelling (FIG. 6c). However, the HAABE derivatives did not induce this swelling reaction even in the presence of 1.0 mM IAABE (FIG. 6c), or in combination with tubulin and tubulin-drug covalent complexes (data reported elsewhere). This was not due to the HAABE derivatives not interacting with tubulin because the tubulin in the outer membrane of mitochondria was shown to be covalently labeled by the same method described in FIG. 4b (data not shown). These results further underline the differences between the mechanism of action of known tubulin ligands and the HAABE derivatives.

Figure 7:
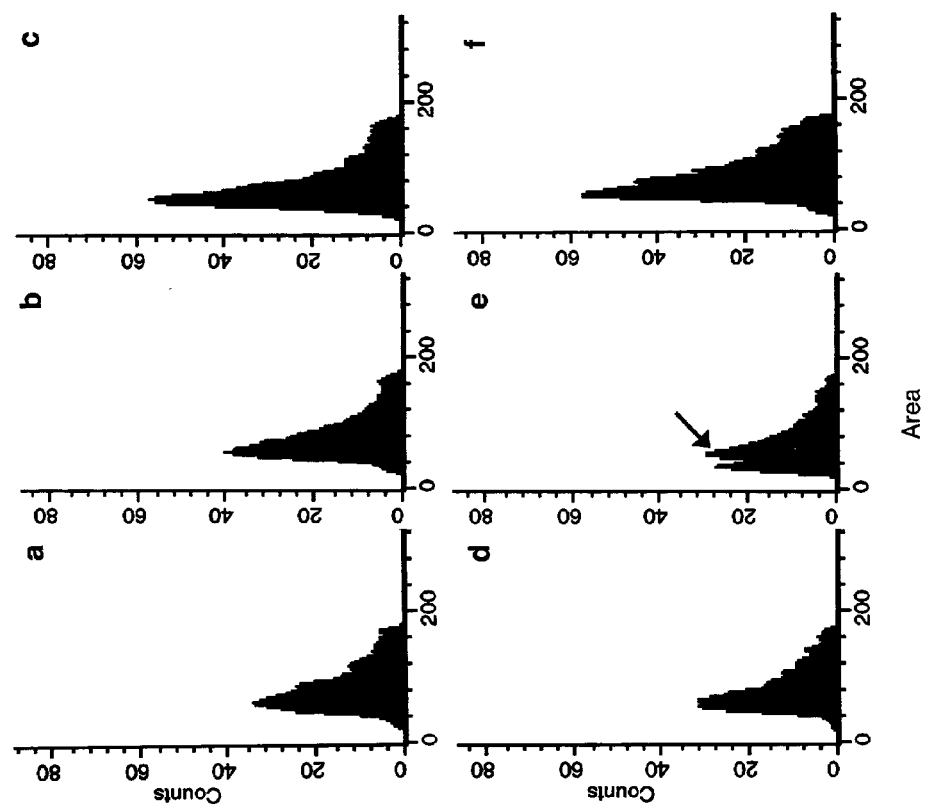
FIG. 7. Effects of the tubulin drug covalent complex (TDCC) on the cell cycle. CEM cells were loaded with tubulin or TDCC by pinocytosis. T=1, 4 and 12 h for tubulin only a,b and c respectively. T=1, 4 and 12 h for TDCC d,e and f respectively. The experiment was performed twice with similar results. Approximately 1000 to 5000 cells were counted per sample. Note the peak at 2.3 n DNA (arrow) in the TDCC sample only.

Our data suggests a novel mechanism of action for a tubulin ligand however we needed to determine whether tubulin was the primary target of IAABE. Therefore, we tested whether the tubulin-drug covalent complex (TDCC) could cause the same cellular response as the compound alone. We purified the TDCC and introduced it into tumor cells by pinocytosis (25). Control cells (tubulin alone) had a rapid reduction in the G0/G1 population from 25 to 15%, also the G2/M population was relatively low which can be expected after the harsh treatment with osmotic modifying solutions (FIG. 7a,b,c). In contrast, TDCC caused the cell cycle to arrest with 2.3 n DNA (FIG. 7d,e,f) and a concomitant decrease in the G0/G1 population as determined by the reduced peak at area=60 units. Cells arrested with 2.3 n DNA are unique to IAABE treated cells (we suggest to call it T2.3 n arrest point or checkpoint), thus we attribute the difference in DNA content profiles to the presence of the complex rather than tubulin alone. The arrested cells in this case did not enter apoptosis within the period of the experiment, probably because the amount of TDCC was limited and could be metabolized by the cells protcolytic machinery (see FIG. 3b, reduction of tubulin label over time). The arrest at G1/S is indicative of the same effect as IAABE alone (FIG. 4) indicating that TDCC can induce the same cell cycle arrest as externally administered IAABE. This data strongly suggests that the primary target of IAABE induced apoptosis is the tubulin molecule.

Growth inhibition assays were used to determine the anti-cancer activity in tissue culture (FIGS. 8,9) and in animal models. Using CEM leukemic cells, the fluorine derivative did not inhibit tumor cell growth at 79 µM, whereas the chlorine, bromine and iodine derivative had $ID_{50}$ values of 7.7+/−0.6, 1.9+/−0.2 and 0.17+/−0.03 respectively. IAABE caused a rapid dissipation of microtubule structures as shown by immunofluorescence staining (FIG. 5). The iodine derivative had broad and potent cancercidal activity as determined by low $ID_{50}$ and $ID_{90}$ activities on multiple cell lines (FIG. 9). The greatest cancercidal activity was on the lymphoma cells (Daudi/wt and Daudi/MDR) where the ratio ($ID_{50}$ normal cells/$ID_{50}$ cancer cells) was upto 500. This compares favorably with vinblastine and paclitaxel which have values of 42 and 24 respectively.

Cell mediated drug resistance from the PGP transporter was tested on the HAABE series, it was shown that PGP(−) cells were just as sensitive as PGP(+) cells (FIG. 9) indicating that this route of drug resistance for vinca-alkaloids and paclitaxel (26,27) does not operate for the HAABE derivatives. These findings are similar to the HAABU derivatives (12,13).

In animal models of clonogenic lymphoma and prostate tumor growth there was significant inhibition of tumor development (FIGS. 10,11). The bromine derivative (BAABE) rendered 80% of EL4 lymphoma implanted mice free of the tumors, compared to all untreated controls which showed large tumor burden under the skin (n=15). In human prostate models the iodine derivative (IAABE) should equivalent tumor inhibition in the short term compared to paclitaxel or vinblastine (see TI% column FIG. 11). In addition, at prolonged times after treatment (90 days) we found that 20% of mice were tumor free with IAABE treatment. Paclitaxel and vinblastine produced no tumor free mice under similar conditions (FIG. 11).

CONCLUSIONS

The HAABEs, being lipophilic, are rapidly taken up by the cell (see FIG. 3: 1 h maximal tubulin labeling), where they bind to tubulin which becomes convalently modified, this has four consequences. First, all the microtubule structures are disassembled. Second, the compounds cannot exit the cell by diffusion or the multi-drug resistance P-glycoprotein pathway, as is the case with other tubulin ligands (28,29). Third, because the compound has a very low to non-existent off-rate for dissociation, the compound has an extremely high apparent-affinity for the target protein. Fourth, the arrest at 2.3 n DNA in the G1/S transition is activated causing the cells to arrest. These effects culminate in apoptosis by a pathway which phosphorylates bcl-2 and converges on the caspase system.

The work described here indicates that TDCC has a profound effect at the arrest at 2.3 n DNA, our model is a checkpoint that relates information to the cell about the ratio of monomer to polymer tubulin. The presence of the TDCC causes an aberrant level of monomeric tubulin thus indicating to the cell that there is insufficient polymer for cellular processes. Presently there is one mechanism that is known to communicate between the tubulin and downstream apoptosis systems, tubulin ligands cause raf-1 kinase to phosphorylate bcl-2 (15,18) which disrupts its association with bax, thus inducing the subsequent steps of apoptosis (22,23). The p53 mediated G1/S checkpoint, which is targeted by DNA alkylating agents (26), is a possible connection to the arrest at 2.3 n DNA because of their temporal location in the cell cycle. It is possible that S100 related proteins such as metastasin and stathmin which are known to bind to p53 and tubulin respectively (29,30) may relate information from the tubulin system to the p53 signaling pathway. It is known that there is cross talk between the S100 family members in terms of expression regulation (31) i.e. downregulation in one family member causes down regulation in another. Thus sequestration of stathmin by TDCC may lead to rapidly reduced levels of the S100 pool (31), and subsequent p53 signaling pathway disruption. In this regard, paclitaxel induces a low percent of normal cells (but not cancer cells) to arrest in the G1 phase (32), suggesting a connection between this G1 phase checkpoint and the arrest at 2.3 n DNA described here.

Tubulin covalently modifying compounds have desirable characters for therapeutic candidates. For example, cells grown in low concentrations of these compounds do not develop resistance (data reported elsewhere, and 33). Other advantages include high affinity and specificity. In addition, the HAABE derivatives differ significantly with respect to other covalently modifying tubulin ligands, especially on cancericidal index, tubulin polymerization profiles, bcl-2 inactivation, cell cycle, DNA synthesis and mitochondrial permeability transition pore complex activation. Finally, the fact that IAABE has a cancericidal index of 500 means that this compound is approaching the efficacy often associated with anti-microbial compounds. Future anti-cancer drug development programs will focus on novel mechanisms to increase potency and decrease side effects, because of their quick absorption, rapid mechanism of action and high specificity we believe that the HAABE derivatives will fill this need.

In addition, the fact that so many other tubulin ligands have applications in anti-restenosis, anti-fungal, anti-helminths and anti-gout chemotherapies there is a strong likelihood that BAABE and IAABE will likewise have potential in other diseases. In support of this hypothesis it was recently found that IAABE has anti-trypanosome activity (ref: Dr. J G Bekesi 1999), following this argument other diseases may be treatable with these compounds.

REFERENCES 1.1 Novel suicide ligands of tubulin arrest cancer cells in S-phase. 1999. A Davis, J-D Jaing, K M Middleton, Y Wang, I Weisz, Y-H Ling and J G Bekesi, Neoplasia, 1 , (6), 498–507.

1.2 Jaing J D, Roboz J, Weisz I, Deng L, Ma L, Holland J F. and Bekesi J G. 1998. Synthesis cancericidal and antimicrotubule activities of 3-haloacetamido-benzoylureas. Anti-Cancer Drug Design, 13 (7), p. 735–747.

1.3 Dumontet C. and Sikie B. 1999. Mechanisms of action of and resistance to anti-tubulin agents: Microtubule dynamics, drug transport and cell death. Review in *J. Clin. Oncol.,* 17, 1061–1070.

1. Not applicable

2. Rowinsky E K. and Donehower R C. 1991. The clinical pharmacology and use of anti-microtubule agents in cancer chemotherapeutics. *Pharmac. Ther.,* 52: 35–84.

3. Wilson L. 1970. Properties of colchicine binding protein from chick embryo brain. Interactions with vinca alkaloids and podophyllotoxin. *Biochem.* 9, 4999–5007.

4. Wilson L. Creswell C R. and Chin D. 1975. The mechanism of action of vinblastine. Binding of [acetyl-3H] vinblastine to embryonic chick brain tubulin and tubulin from sea urchin sperm tail outer doublet microtubules. *Biochem.*, 14, 5586–5592.

5. Malawista S E, Bensch K G. and Sato H. 1968. Vinblastine and griseofulvin reversibly disrupt the living mitotic spindle. *Science.* 160: 770–772.

6. George P, Journey L J. and Goldstein M N. 1965. Effect of vincristine on the fine structure of Hela cells during mitosis. *J. Natl. Cancer Inst.*, 35, 355.

7. Schiff P B. and Horwitz S B. 1979. Promotion of microtubule assembly in vitro by taxol. *Nature,* 277, 665.

8. Schiff P B, Fant J. and Horwitz S B. 1980. Taxol stabilizes microtubules in mouse fibroblast cells. *Proc. Natl. Acad. Sci. USA.*, 77, 1561.

9. Sandercock J, Parmar M K and Torri V. 1998. First-line chemotherapy for advanced ovarian cancer: paclitaxel, cisplatin and the evidence. *Br. J. Cancer.* 78, 1471–1478.

10. Miller K D, Sledge Jr. G W, 1999. Taxanes in the treatment of breast cancer: A prodigy comes of age. *Cancer Invesiig.*, 17, 121–136.

11. Jordan M A. and Wilson L. 1998. Microtubules and actin filaments: dynamic targets for cancer chemotherapy. *Curr. Op. Cell Biol.*, 10, 123–130.

12. Jiang J D, Wang Y, Roboz J. Strauchen J. Holland J F. and Bekesi J G. 1998. Inhibition of microtubule assembly in tumor cells by 3-bromoacetylamino benzoylurea, a new cancericidal compound. *Cancer Res.*, 58, 2126–2133.

13. Jiang J D, Davis A S. Middleton K M, Ling Yi-He, Perez-Soler R, Hollan J F. and Bekesi J G. 1998. 3-(Iodoacetamido)-benzoylurea: A novel cancericidal tubulin ligand that inhibits microtubule polymerization, phosphorylates bcl-2, and induces apoptosis in tumor cells. *Cancer Res.*, 58, 5389–5395.

14. Luduena R F. and Roach M C. 1981. Interaction of tubulin with drugs and alkylating agents. 2. Effects of colchicine, podophyllotoxin and vinblastine on the alkylation of tubulin. *Biochem.*, 20, 444–4450.

15. Halder S, Chintapalli J. and Croce C M. 1996. Taxol induced bcl-2 phosphorylation and death of prostate cancer cells. *Cancer Res.* 56, 1253–1255.

16. Ling Y H, Consoli U, Tornos C, Andreeff M, Perez-Soler R. 1998. Accumulation of cyclin B1, activation of cyclin B1-dependent kinase and induction of programmed cell death in human epidermoid carcinoma KB cells treated with toxal. *Int. J. Cancer,* 75: 925–932.

17. Halder S, Basu A. and Croce C M. 1997. Bcl-2 is the guradian of microtubule integrity. *Cancer Res.* 57, 229–233.

18. Blagosklonny M V, et al. 1997. Raf1/bcl-2 phosphorylation: a step from microtubule damage to cell death. *Cancer Res.* 57, 130–135.

19. Yang J, et al. 1997. Prevention of apoptosis by Bcl-2: release of cytochrome c from mitochondria blocked. *Science,* 275, 1129–1132.

20. Kluck R M, Bossy-Wetzel E, Green D R. and Newmeyer D D. 1997. The release of cytochrome c from mitochondria: a primary site for bcl-2 regulation of apoptosis. *Science,* 275, 1132–1136.

21. Costantini P, Petronilli V, Colona R. and Bernardi P. 1995. On the effects of paraquat on isolated mitochondria. Evidence that paraquat causes opening of the cyclosporin A-sensitive permeability transition pore synergistically with nitric oxide. *Toxicol.,* 99, 77–88.

22. Marchetti P, et al.. 1996. Mitochondrial permeability transition is a central coordinating event of apoptosis. *J. Exp. Med.,* 183: 1155–1160.

23. Zamzami N, et al. 1996. Mitochondria control of nuclear apoptosis. *J. Exp. Med.* 183: 1533–1544.

24. Evtodienko Y V, et al. 1996. Microtubule-active drugs suppress the closure of the permeability transition pore in tumour mitochondria. *FEBS Letts,* 393, 86–88.

25. Okada C Y and Rechsteiner M. 1982. Introduction of macromolocules into cultured mammalian cells by osmotic lysis of pinocytic vesicles. *Cell,* 29, 33–41.

26. Brown J M. And Wouters B G. 1999. Apoptosis, p53, and tumor cell sensitivity to anticancer agents. *Cancer Res,* 59, 1391–1399.

27. Huang, Y., Ibrado, A. M., Reed, J. C., Bullock, G., Ray, S., Tang, C. and Bhalla, K. Co-expression of several molecular mechanisms of multidrug resistance and their significance for paclitaxel cytotoxicity inhuman AML HL-60 cells. *Leukemia* 11: 253–257, 1997.

28. Dey, S., Ramachandra, M., Pastan, I., Gottesman, M. M. and Ambudkar, S. V. 1997. Evidence for two nonidentical drug-interaction sites in the human P-glycoprotein. *Proc. Natl. Acad. Sci. USA.* 94: 10594–10599.

29. Parker C, Lakshmi M S, Piura B. and Sherbet G V. 1994. Metastasis associated mts1 gene expression correlates with increased p53 detection in B16 murine melanoma. *DNA Cell. Biol.* 13, 343–351.

30. Marklund U, Larsson N, Gradin H M, Brattsand G. and Gullberg M. 1996. Oncoprotein 18 is a phosphorylation responsive regulator of microtubule dynamics. *EMBO J.* 15, 5290–5298.

31. Sherbet G V. and Lakshmi M S. 1998. S100A4 (MTS1) calcium binding protein in cancer growth, invasion and metastasis. *Anticancer Res.*, 18, 2415–2422.

32. Trielli M O, Andreassen P R, Lacroix F B and Margolis R L. 1996. Differential taxol-dependent arrest of transformed and non-transformed cells in the G1 phase of the cell cycle, and specific-related mortality of transformed cells. *JCB,* 135, 689–700.

33. Shan B, et al. 1999. Selective, covalent modification of beta-tubulin residue Cys-239 by T138067, an antitumor agent with in vivo efficacy against multidrug resistant tumors. *Proc. Natl. Acad. Sci. USA.* 96, 10, 5686–90.

34. Banjeree R, et al. 1992. Productive non-lytic HIV-1 replication in a newly established human leukemia cell line. *Proc. Natl. Acad. Sci. USA,* 89, 9996–1000.

35. Bekesi J G, et al. 1995. Translocation of cytoplasmic antigen markers in a biphenotypic cell line derived from a patient with myelodysplasis syndrome. *Mol. Cell. Differ.* 3, 111–123.

36. Davis A S. and Middleton K M. 1998. Lyophilized tubulins. U.S. patent application Ser. No. 09/310,981. Patent pending.

The invention claimed is:

1. A method of inhibiting cell division comprising contacting a cell with an effective amount of 3-iodoacetamido benzoyl ethyl ester (3-IAABE), wherein the cell is selected from a leukemia cell, a melanoma cell, a renal cancer cell, a breast cancer cell, a non-small cell lung cancer cell, a colon cancer cell, a prostate cancer cell, and a lymphoma cell.

2. The method of claim 1 wherein the cell is contacted with 0.005 to 0.51 μg/ml of 3-IAABE.

3. The method of claim 1 wherein the cell is a prostate cancer cell.

4. The method of claim 1 wherein the cancer cell is a lymphoma cell.

5. The method of claim 1 wherein the cell is a colon cancer cell.

6. The method of claim 1 wherein the cell is a non-small cell lung cancer cell.

7. The method of claim 1 wherein the cell is a breast cancer cell.

8. The method of claim 1 wherein the cell is a renal cancer cell.

9. The method of claim 1 wherein the cell is a melanoma cell.

10. The method of claim 1 wherein the cell is a leukemia cell.

* * * * *